United States Patent [19]

Coughenour et al.

[11] Patent Number: 4,754,095
[45] Date of Patent: Jun. 28, 1988

[54] CHEMICAL CONVERSION PROCESS

[75] Inventors: Glenn E. Coughenour, Bryn Mawr; John C. Jubin, Jr., Wallingford, both of Pa.

[73] Assignee: Atlantic Richfield Company, Los Angeles, Calif.

[21] Appl. No.: 601,141

[22] Filed: Apr. 16, 1984

[51] Int. Cl.$^4$ .............................................. C07C 2/00
[52] U.S. Cl. ..................................... 585/500; 585/301; 585/654; 585/656; 585/901
[58] Field of Search ............... 585/901, 301, 654, 656, 585/500

[56] References Cited

U.S. PATENT DOCUMENTS

| | | | |
|---|---|---|---|
| 4,144,277 | 3/1979 | Walker et al. | 585/656 |
| 4,152,393 | 5/1979 | Callahan et al. | 585/656 |
| 4,205,194 | 5/1980 | Mitchell, III et al. | 585/500 |
| 4,319,984 | 3/1982 | Pellet et al. | 208/139 |
| 4,443,649 | 4/1984 | Jones et al. | 585/500 |
| 4,450,310 | 5/1984 | Fox et al. | 585/500 |
| 4,454,363 | 6/1984 | Teng et al. | 585/428 |

Primary Examiner—William R. Dixon, Jr.
Assistant Examiner—James M. Hunter, Jr.
Attorney, Agent, or Firm—Craig E. Larson

[57] ABSTRACT

A method is disclosed in which a first gas is contacted with a solid at an elevated reaction temperature to produce a gaseous product, the solid being deactivated during said contact and further, being exothermically reactivated by a second gas, the improvement which comprises providing the solids in at least three reactor zones and sequantically operating each reactor according to the cycle: reaction/reactant preheat/solids reativation. Preferaly the reactors are operated concurrently such that, at any time, at least one reactor is producing product and at least one reactor is preheating reactant to reaction temperature.

10 Claims, No Drawings

CHEMICAL CONVERSION PROCESS

BACKGROUND OF THE INVENTION

1. Field of the Invetion

This invention relates to chemical conversions that involve processes wherein solids and fluids are contacted to effect the desired conversion. More particularly, this invention relates to chemical conversion of gaseous hydrocarbons. One particular embodiment of this invention relates to the synthesis of hydrocarbons from a methane source. Another particular embodiment of this invention relates to dehydrogenation of hydrocarbons.

2. Fixed Bed Reactor Systems

A wide variety of chemical conversions are known wherein fluid reactants are contacted with solids, the solids either functioning as catalysts to promote the conversion of reactants to desired products or functioning as a reactant (or both). Typically, the solids in such processes, whether functioning as catalysts or as reactants, require periodic replenishment or regeneration.

A preferred means for conducting many such industrial chemical processes involves the use fluidized beds of solids with circulation of solids between reaction and regeneration zones. While ideally suited for many chemical conversions, circulating solids systems have limitations restricting their usefulness in particular applications. For example, as the period between successive replenishment/regeneration and reaction steps decreases, increasingly larger amounts of solids must be moved within the system, vastly increasing the cost and complexity of the reaction system. As a further example, chemical conversions requiring relatively severe operating conditions (especially those requiring high temperatures) may adversely effect the physical or other properties of the solid, which in turn adversely effect the solid's fluidization characteristics.

Thus, despite the widespread use of fluidized bed or other moving bed systems in fluid-solid contacting, chemical conversion processes, fixed bed systems remain important to a substantial number of chemical processes. See, for example, U.S. Pat. No. 4,406,777 which describes a number of problems encountered with fixed bed reactor systems involving gradually deactivating solids and solutions proposed therefore.

In addition, when used for exothermic chemical conversions, removal of heat from fixed beds of solids is difficult without causing prohibitive temperature gradients in the reactor beds. Use of tubular reactors may overcome this difficulty, but improved systems are desirable.

3. Synthesis of Hydrocarbons from a Methane Source

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons carbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion of olefins such as ethylene or propylene would be extremely valuable to the chemical industry.

Recently, it has been discovered that methane may be converted to higher hydrocarbons (e.g., ethane, ethylene and higher homologs) by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regenerating of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See commonly-assigned U.S. Pat. Nos. 4,443,644; 4,443,645; 4,443,646; 4,443,647; 4,443,648; 4,443,649; and 4,444,984 the entire contents of each being incorporated herein by reference.

Commonly-assigned U.S. patent application Ser. No. 522,935, filed Aug. 12, 1983, discloses and claims a process which comprises contacting methane with an oxidative synthesizing agent under elevated pressure (e.g., 2–100 atmospheres) to produce greater amounts of $C_3+$ hydrocarbon products.

Commonly-assigned U.S. patent application Ser. No. 522,938, filed Aug. 12, 1983, discloses and claims a process for the conversion of methane to higher hydrocarbons which comprises contacting methane with particles comprising an oxidative synthesizing agent which particles continuously recirculate between two physically separate zones—a methane contact zone and an oxygen contact zone.

Commonly-assigned U.S. patent application Ser. No. 522,937, filed Aug. 12, 1983, discloses and claims a process for the conversion of methane to higher hydrocarbons which comprises contacting methane with an oxidative synthesizing agent containing a promoting amount of alkali metal and/or compounds thereof.

Commonly-assigned U.S. Pat. No. 4,945,374, discloses and claims a process for the conversion of methane to higher hydrocarbons which comprises contacting methane with an oxidative synthesizing agent containing a promoting amount of alkaline earth metal and/or compounds thereof.

Commonly-assigned U.S. patent application Ser. No. 600,665 filed Apr. 16, 1984 discloses and claims a process for the conversion of methane to higher hydrocarbons which comprises contacting methane with a contact solid comprising a reducible oxide of praseodymium and at least one member of the group consisting of alkali metals, alkaline earth metals, and compounds thereof.

Commonly-assigned U.S. patent application Ser. No. 600,918 filed Apr. 16, 1984, now abandoned discloses and claims a process for the conversion of methane to higher hydrocarbons which comprises contacting methane with a contact solid comprising a reducible oxide of terbium and at least one member of the group consisting of alkali metals, alkaline earth metals, and compounds thereof.

Commonly-assigned U.S. patent application Ser. No. 600,917, filed Apr. 16, 1984 discloses and claims a process for the conversion of methane to higher hydrocarbons which comprises contacting methane with a contact solid comprising a reducible oxide of cerium and at least one member of the group consisting of alkali metals, alkaline earth metals, and compounds thereof.

Commonly-assigned U.S. patent application Ser. No. 600,730 filed Apr, 16, 1984, now abandoned discloses and claims a process for the conversion of methane to higher hydrocarbons which comprises contacting methane with a contact solid comprising a reducible oxide of iron and at least one member of the group consisting of alkali metals, alkaline earth metals, and compounds thereof.

Commonly-assigned U.S. Pat. No. 4,489,215 discloses and claims a process for the conversion of methane to higher hydrocarbons which comprises contacting methane with a contact, solid comprising a reducible oxide of ruthenium and at least one member of the group consisting of alkali metals, alkaline earth metals, and compounds thereof.

4. Dehydrogenation of Hydrocarbons

Various processes for the dehydrogenation of hydrocarbons are known. Such processes seek to produce olefins and/or dienes from alkanes or to produce dienes from olefins. More conventional dehydrogenation processes include thermal or catalytic dehydrogenation. More recently, oxidative dehydrogenation processes have been introduced. See generally McKetta, J. J., et al., *Encyclopedia of Chemical Processing and Design*, Vol. 5, pages 127-139 (Marcel Dekker, N.Y., N.Y. 1977) (discusses various dehydrogenation processes in the context of butadiene manufacturing).

In the oxidative dehydrogenation process, hydrogen is removed from a hydrocarbon by oxygen, forming water. Oxydehydrogenation catalysts have been made from a variety from metal oxides and salts.

5. Objects of the Invention

It is an object of this invention to provide a reactor system, especially one having enhanced capabilities for the removal and utilization of heat generated by exothermic chemical conversions.

It is another object of this invention to provide an improved process for the chemical conversion of hydrocarbons.

It is a further object of this invention to provide a process for the synthesis of hydrocarbons from a methane source.

It is still a further object of this invention to provide a process for the dehydrogenation of hydrocarbons.

Other aspects, objects and the several advantages of this invention will become apparent to those skilled in the art upon reading this disclosure and the appended claims.

SUMMARY OF THE INVENTION

In accordance with the present invention, a chemical conversion process is provided wherein a reactant is contacted with fixed beds of solids to effect the desired conversion. The process is characterized by rapid deactivation of the solids (the solids functioning as a catalyst and/or a reactant), and an exothermic reactivation of the solids.

More particularly, this invention relates to an improvement in chemical conversion processes of the type wherein a reactant is contacted with a solid at an elevated reaction temperature to produce a reaction product, said solid being rapidly deactivated during said contact, and said deactivated solid being reactivated by contact with a reactivating gas under exothermic conditions and again contacted with said reactant, said improvement comprising:

(a) providing a quantity of solids in relatively equal amounts in at least three reactor zones;

(b) sequentially operating each reactor zone according to the cycle comprising (1) introducing said reactant, preheated to reaction temperature, into the reactor and withdrawing reaction product from the reactor; (2) preheating said reactant to reaction temperature by introducing said reactant into the reactor and withdrawing preheated reactant from the reactor; (3) reactivating deactivated solids by introducing said reactivating gas into the reactor and withdrawing gaseous effluent from the reactor; and (c) concurrently operating said reactors such that at any given time, the reactant is being preheated to reaction temperature in a first reactor and said preheated reactant is being converted into said reaction product in a second reactor.

As will be apparent to one skilled in the art it will generally be desirable to purge the reactors between the reaction and preheating steps of the cycle and between the reactivation and reaction steps of the cycle. Such is within the scope of the present invention.

In one specific embodiment of the process of this invention the chemical conversion process is a method for converting methane to higher hydrocarbon products which comprises contacting methane at a reaction temperature, preferably within the range of about 500° to 1000° C., with a quantity of solids comprising at least one reducible oxide of at least one metal which oxides are reduced when contacted with methane and produce higher hydrocarbon products and water and wherein solids comprising reduced metal oxides are periodically contacted with a oxygen-containing gas to regenerate solids comprising said reducible oxides.

In another specific embodiment of the process of this invention, the chemical conversion process is a method for dehydrogenating hydrocarbons which comprises: (1) contacting the hydrocarbon with an oxidative dehydrogenation agent to form water and dehydrogenated hydrocarbon products and (2) contacting deactivated oxidative dehydrogenation agent with an oxygen-containing gas to reactivate the agent.

DETAILED DESCRIPTION OF THE INVENTION

1. Chemical Conversion Process

In its broader aspects, the process of the present invention includes improved methods for performing a variety of chemical conversions, and therefore, the following, more detailed description of specific embodiments of this broader process are intended to be illustative but not limiting of the claimed process.

As previously noted, the process is generally concerned with problems arising when conducting a certain class of chemical conversions. One characteristic of this class is that a gaseous reactant is contacted with a solid at an elevated reaction temperature. By "elevated reaction temperature" is meant a temperature greater than ambient. More typically, the temperature will be above 200° C. The function of the solid in the conversion process is not narrowly critical. Generally however, it effects the conversion by functioning as a catalyst or as a reactant or both.

A second characteristic of the class of chemical conversions to which this invention pertains is that conversion of gaseous reactant may occur under a fairly wide temperature range without adversely affecting nonselective reactions. The overall conversion may be endothermic or exothermic without effecting the suitability of applying the method of this invention.

A third characteristic is that the solid is deactivated during conversion of the gaseous reactant. Any process wherein the solid may be considered a reactant will fulfill this characteristic.

A fourth characteristic is that the deactivated solid is periodically contacted with a reactivating gas to reactivate the solid. It is the exothermic nature of this reactivation and the consequent non-isothermal behavior of the overall process which present a principle problem addressed by this invention: removal of heat from the fixed bed reactors without causing prohibitive temperature gradients in the reactor beds. Use of tubular reactors coupled with indirect heat exchange means has been previously employed in this context. The present invention overcomes the heat problem without the need to employ tubular reactors. In a typical application of the process of this invention, the reactivating gas will be an oxygen-containing gas but the broader embodiments of this invention are not so limited. Best applications of this process are made in conversion processes wherein solid reactivation is exothermic.

Suitable applications of the broader process of this invention will be apparent to one skilled in the art. The operation of the process and its various advantages are illustrated by its more specific embodiments.

2. Synthesis of Hydrocarbons from a Methane Source

One highly advantageous application of the general process of this invention is the conversion of methane to higher hydrocarbons. More particularly this aspect of the invention relates to an improvement in a method for converting methane to higher hydrocarbon wherein a gas comprising methane is contacted at a reaction temperature within the range of about 500° to 1000° C. with a quantity of solids comprising at least one reducible oxide of at least one metal which oxides are reduced when contacted with methane and produce higher hydrocarbon products and water and wherein solids comprising reduced metal oxides are periodically contacted with an oxygen-containing gas to regenerate solids comprising said reducible oxides, said improvement comprising:

(a) providing a quantity of solids in relatively equal amounts in at least three reactor zones;

(b) sequentially operating each fixed reactor zone according to the cycle comprising: (1) introducing a gas comprising methane, preheated to reaction temperature, into a reactor and withdrawing gaseous reaction products comprising higher hydrocarbons from the reactor; (2) preheating said gas comprising methane to reaction temperature by introducing said gas into the reactor and withdrawing preheated gas comprising methane from the reactor; and (3) regenerating solids comprising reducible metal oxides by introducing an oxygen-containing gas the reactor and withdrawing gaseous effluent from the reactor; and (c) concurrently operating said reactors such that at any give time, the gas comprising methane is being preheated to reaction temperature in a first reactor, and said preheated gas comprising methane is being converted into hydrocarbon products in a second reactor.

Preferably, gas comprising methane is purged from the cooled solids after the methane preheating step and before the solids regeneration step. Also, oxygen-containing gas is preferably purged from the solids after the solids regeneration and before the methane reaction step. Purging the reactor may be easily accomplished by passing a gaseous material such as nitrogen or steam through the solids.

In addition to methane the feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The solid which is contacted with methane in the first stage of the present process has heretofore been generally referred to as an oxidative synthesizing agent. Oxidative synthesizing agents comprise at least one oxide of at least one metal, which oxides when contacted with methane at temperatures selected within the range of about 500° to 1000° C. produce higher hydrocarbon products, coproduct water and a reduced metal oxide. The composition thus contains at least one reducible oxide of at least one metal. The term "reducible" identifies those oxides of metals which are reduced by the methane contact. The term "oxide(s) of metal(s)" includes: (1) one or more metal oxides (i.e., compounds described by the general formula $M_xO_y$ wherein M is a metal and the subscripts x and y designate the relative atomic proportions of metal and oxide in the composition) and/or (2) one or more oxygencontaining metal compounds, provided that such oxides and compounds have the capability of performing to produce higher hydrocarbon products as set forth herein.

Effective agents for the conversion of methane to higher hydrocarbons have previously been found to comprise reducible oxides of metals selected from the group consisting of manganese, tin, indium, germanium, antimony, lead, bismuth and mixtures thereof. Alkali and alkaline earth metals and compounds have been found to improve the hydrocarbon product selectivity of these agents. The further incorporation of phosphorus into agents promoted by alkali or alkaline earth components enhances catalyst stability.

Reducible oxides of cerium, praseodymium, and terbium have also been found to be effective for the conversion of methane to higher hydrocarbons when the rare earth component is associated with an alkali or alkaline earth metal component.

The metal components may be associated with other support materials such as silica, magnesia, alumina, titania, zirconia and the like and combinations thereof. When employing agents containing rare earth components—oxides of Ce, Pr and Tb—the rare earth oxides preferably serve as supports.

Reducible oxides of manganese have been found to be particularly desirable for methane conversion, especially when associated with an alkali metal (preferably sodium). Especially preferred agents comprise silica- and/or magnesia supported agents containing oxides of manganese and sodium.

The agent contacted with methane in the first step of the present invention can be prepared by any suitable method. Conventional methods such as precipitation, coprecipitation, impregnation or dry mixing can be used. Supported solids may be prepared by methods such as adsorption, impregnation, precipitation, coprecipitation, and dry mixing. When phosphorus is incorporated into the agent, it is desirable to provide it in the form of a phosphate of an alkali or alkaline earth metal.

A suitable method of preparation is to impregnate a support with solutions of the desired metals. Suitable compounds useful for impregnation include the acetates, acetylacetonates, oxides, carbides, carbonates, hydroxides, formates, oxalates, nitrates, phosphates, sulfates, sulfides, tartrates, fluorides, chlorides, bromides, or iodides. After impregnation the preparation is dried to remove solvent and the dried solids calcined, preferably in air, at a temperature within the range of about 300° to 1200° C. Particular calcination temperatures will vary depending upon the particular metal compound or compounds employed.

Regardless of how the components of the agent are combined, the composite will be dried and calcined at elevated temperatures prior to use of the process of this invention.

Preferably, methane is contacted with the agent in the substantial absence of catalytically effective nickel, noble metals and compounds thereof (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the first step of this invention relative to such contacting in the absence of such metals and compounds thereof.

Operating temperatures for the first step of the method of this invention are generally within the range of about 500° to 1000° C. If reducible oxides of metals such as In, Ge or Bi are present in the solid, the particular temperature selected may depend, in part, on the particular reducible metal oxide(s) employed. Thus, reducible oxides of certain metals may require operating temperatures below the upper part of the recited range to minimize sublimation or volatilization of the metals (or compounds threof) during methne contact. Examples are: (1) reducible oxides of indium, (operating temperatures will preferably not exceed about 850° C.); (2) reducible oxides of germanium (operating temperatures will preferably not exceed about 850° C.); and (3) reducible oxides of bismuth (operating temperatures will preferably not exceed about 850° C.).

Operating pressures for the methane contacting step are not critical to the presently claimed invention. However, both general system pressure and partial pressure of methane have been found to effect overall results. Preferred operating pressures are within the range of about 1 to 30 atmospheres.

Contacting methane and a reducible metal oxide to form higher hydrocarbons from methane also produces a reduced metal oxide and co-product water. The exact nature of the reduced metal oxides are unknown, and so are referred to herein as "reduced metal oxides". Regeneration of a reducible metal oxide is readily accomplished by contacting such reduced materials with oxygen (e.g., an oxygen-containing gas such as air) at elevated temperatures, preferably at a temperature selected within the range of about 300° to 1200° C., the particular temperature selected depending on the metal(s) included in the solid.

In applying the general method of this invention to the synthesis of hydrocarbons from methane, at least one module consisting of at least three fixed bed reactors will be employed. At any given time, at least one reactor in the module is preheating methane, at least one reactor in the module is converting methane to higher hydrocarbons and (preferably) at least one reactor in the module is regenerating. Other parallel modules may be provided and, within any module, other reactors may be operating at any given point in the above-described cycle.

In a preferred embodiment of this aspect of the method of the method of this invention, a module consists of four reactor units, in one reactor preheating methane, one reactor converting methane to higher hydrocarbons, one reactor regenerating, and one reactor being purged. The methane conversion step is slightly exothermic but the regeneration step is very exothermic. Heat is removed by feeding gas comprising methane and oxygen-containing gas to the reactor system at temperatures below reaction temperature. These feed temperatures may be adjusted to provide the desired heat balance and temperature profiles for the reactor system.

One particular embodiment of the general method of this invention is disclosed in U.S. patent application Ser. No. 601,143 filed Apr. 16, 1984 the entire content of which is incorporated herein by reference. However, the present invention embraces other embodiments as well.

In part, this invention is based on the use of direct reactant/solids contacting to control the reactor zone temperature and to efficiently provide heat to the reactant being fed to the process. While solids may be provided as fixed beds in the reactor zones of the present process, solids may also be provided as fluidized, ebullating, moving or entrained beds of solids. What distinguishes the present method, in part, is the fact that solids do not "circulate" between reaction and regeneration zones. Rather, the solids are maintained within one zone operated according to the specific reaction/preheat/regeneration cycle of this invention.

In one presently preferred embodiment of this invention, solids are provided as fixed fluidized beds in each reactor zone. Such an embodiment offers an advantage over use of fixed beds in that heat transfers within the reactor zones is facilitated, allowing maintenance of a more uniform temperature profile within the reactor zone.

3. Dehydrogenation of Hydrocarbons

Dehydrogenation of normally gaseous and light liquid hydrocarbons to less saturated hydrocarbons is a well-known process. Paraffins are dehydrogenated to produce olefins and certain olefins are dehydrogenated to produce diolefins. Butadiene for example may be produced by dehydrogenating butylene from any selected source such as the butylenes obtained from the dehydrogenation of butane.

The general process of the present invention is application to dehydrogenation processes wherein a dehydrogentable hydrocarbon is contacted with an oxidative dehydrogenation agent (or catalyst) to produce a dehydrogenated hydrocarbon product. The catalyst may be any of a number of metal oxide or metal salt catalysts exemplified by bismuth-molybdate, magnesium-chromium-ferrite and manganese-ferrite.

Oxidative dehydrogenation agents are compositions comprising at least one oxide of at least one metal, which compositions, when contacted with a dehydrogenatable hydrocarbon (preferably at a temperature selected within the range of about 500° to 1000° C.), produces dehydrogenated hydrocarbon products, co-product water, and a composition comprising a reduced metal oxide. The composition thus contains at least one reducible oxide of at least one metal. The term "reducible" is used to identify those oxides of metals which are reduced by contact with dehydrogenatable hydrocarbons at elevated temperatures (preferably selected within the range of about 500° to 1000° C.). The term "oxide(s) of metal(s)" includes (1) one or more metal oxides (i.e., compounds described by the general formula $M_xO_y$ wherein M is a metal and the subscripts x and y designate the relative atomic proportions of metal and oxygen in the compound) and/or (2) one or more oxygen-containing metal compounds, provided that such oxides and compounds have the capability of performing to dehydrogenate dehydrogenatable hydrocarbons as set forth herein.

One class of preferred oxidative dehydrogenation agents comprises reducible oxides of metals selected from the group consisting of Mn,Sn,In,Ge,Sb,Pb, Bi, and mixtures thereof. Particularly preferred oxidative dehydrogenation agents comprise a reducible oxide of manganese and mixtures of reducible oxides of manganese with other oxidative dehydrogenation agents. More particularly preferred are reducible oxides of manganese associated with a silica support. See concurrently filed U.S. patent application Ser. No. 600,916 filed Apr. 16, 1984 the entire content of which is incorporated herein by reference.

Another class of preferred oxidative dehydrogenation agents comprise a reducible metal oxide and a promoting amount of an alkali and/or alkaline earth metal component. A particularly preferred member of this class of agents comprises a reducible metal oxide and a promoting amount of an alkali metal associated with a support comprising an alkaline earth metal and/or compound thereof. More particularly preferred are solids comprising a reducible oxide of Mn, Na and/or a compound thereof, and a support comprising magnesia. See concurrently currently filed U.S. patent application Ser. No. 600,655 filed Apr. 16, 1984, the entire content of which is incorporated herein by reference.

Still another class of preferred oxidable dehydrogenation agents comprises: (1) reducible oxides of metals selected from the group consisting of Pr, Tb and Ce, and (2) at least one member of the group consisting of alkali metals, alkaline earth metals and compounds thereof. See concurrently filed U.S. Pat. Nos. 600,735; 600,652; and 600,651, each filed on Apr. 16, 1984, the entire contents of which are incorporated herein by reference. Reducible oxides of Pr and Tb are particularly preferred members of this class of agents. Reducible oxides of Pr are still more particularly preferred. Especially preferred members of this class are agents wherein the said reducible oxides are provided as supports for the other components of the agent.

A still further class of preferred oxidative dehydrogenation agents comprises: (1) reducible oxides of metals selected from the group consisting of Fe and Ru and (2) at least one member of the group consisting of alkali metals, alkaline earth metals and compounds thereof. See concurrently filed U.S. patent application Ser. Nos. 600,734 and 600,736, each filed on Apr. 16,1984, the entire contents of which are incorporated herein by reference. Reducible oxides of Fe are, currently, a particularly preferred member of this class of agents. Also particularly preferred are agents wherein the said reducible oxides are provided as supports or the other components of the agent.

Other oxidative dehydrogentation agents may also be employed in the method of this invention, as will be apparent to one skilled in the art.

In the present invention, reducible oxides are provided as solid particles. They may be supported by, or diluted with, a conventional support material such as silica, alumina, titania, zirconia, and the like, and combinations thereof. A presently preferred support is silica.

Supported solids (i.e., particles) can be prepared by any suitable method. Conventional methods such as adsorption, impregnation, precipitation, coprecipitation, or dry-mixing can be used. A suitable method is to impregnate the support with solutions of compounds of the desired metal. Some examples of suitable compounds are the acetate, acetylacetonate, oxide, carbide, carbonate, hydroxide, formate, oxalate, nitrate, phosphate, sulfate, sulfide, tartrate, fluoride, chloride, bromide or iodide. After impregnation, the preparation is dried in an oven to remove solvent and the dried solid is prepared for use by calcining, preferably in air, at temperatures selected within the range of about 300° to 1200° C. Particular calcination temperatures will vary depending upon the particular metal compound.

Metal loadings on supported solids will generally be within the range of about 1 to 50 wt. % (calculated as the elemental metal(s) of the reducible oxides(s)).

The dehydrogentable hydrocarbon feedstock employed in the method of this invention is intended to include a wide variety of hydrocarbons; e.g., $C_2+$ alkanes, cycloalkanes, olefins, alkylaromatics, etc. The dehydrogenated product will of course depend in part on the feedstock selected. For example, alkanes may be dehydrogenated to form olefins, diolefins, alkynes, etc., and olefins may be dehydrogenated to form diolefins, alkynes, etc. Thus, potential uses for the present process include the following conversions:

(1) ethane→ethylene→acetylene;
(2) propane→propylene;
(3) butane→butene→butadiene;
(4) 2-methylbutane→2-methylbutenes→isoprene; and
(5) toluene→stilbene.

One preferred class of feedstocks comprises $C_2$–$C_5$ alkanes.

Operating temperatures for the contacting of hydrocarbon-containing gas and the particles comprising an oxidative dehydrogenating agent are preferably selected from the range of about 500° to 1000° C., the particular temperature selected depending upon the metal oxides employed in the oxidative dehydrogenation agent. For example, all oxidative dehydrogenation (defined above) agents have the capability of dehydrogenating hydrocarbons when the temperature of the hydrocarbon contact is selected within the lower part of the recited range. Reducible oxides of certain metals, however, may require operating temperatures below the upper part of the recited range to minimize sublimation or volatilization of the metals (or compounds thereof) during hydrocarbon contact. Examples are: (1) reducible oxides of indium (operating temperatures will preferably not exceed about 850° C.); (2) reducible oxides of germanium (operating temperatures will preferably not exceed about 800° C.); and (3) reducible oxides of bismuth (operating temperatures will preferably not exceed about 850° C.).

Operating pressures for the hydrocarbon contacting step are not critical to the presently claimed invention.

Contacting hydrocarbon and an oxidative dehyrogenation agent to dehyrogenate dehydrogenatable hydrocarbons also reduces the oxidative dehydrogenation agent and produces coproduct water. The exact nature of the reduced forms of oxidative dehydrogenation agents are unknown, and so are referred to herein as "reduced dehydrogenation agent" or as "a reduced metal oxide." Regeneration of a reducible metal oxide is readily accomplished by contacting reduced compositions with oxygen (e.g., an oxygen-containing gas such as air) at a temperature selected within the range of about 300° to 1200° C., the particular temerature selected depending on the metal(s) included in the oxidative dehydrogenation agent.

In applying the general method of this invention to the dehydrogenation of dehydrogenatable hydrocarbons, at least one module consisting of at least three fixed bed reactors will be employed. At any given time, at least one reactor in the module is preheating hydrocarbons, at least one reactor in the module is dehydrogenating hydrocarbons to dehydrogenated hydrocarbons and (preferably) at least one reactor in the module is regenerating. Other parallel modules may be provided and, within any module, other reactors may be operating at any given point in the above described cycle. Operation of the reactor system to dehydrogenate hydrocarbons is analogous to the methane conversion process already described. Since the dehydrogenation reactions may be more endothermize than the methane conversion reactions, higher preheat temperatures or dehydrogenatable hydrocarbons may be desirable. Also, because of different relative reaction rates of the hydrocarbon contacting step and the regeneration step, a different number of reactors per module and different cycle times may be desirable for hydrocarbon dehydrogenation.

What is claimed is:

1. In a chemical conversion process wherein a gaseous reactant is contacted with a solid at an elevated reaction temperature to produce a gaseous reaction product, said solid being deactivated during said contact, and said deactivated solid being reactivated by contact with a reactivating gas under exothermic conditions and again contacted with said gaseous reactant, the improvement which comprises:
    (a) providing a quantity of solids in relatively equal amounts in at least three reactor zones;
    (b) sequentially operating each reactor zone according to the cycle comprising: (1) introducing said gaseous reactant, preheated to reaction temperature, into the reactor and withdrawing gaseous reaction product from the reactor; (2) preheating said gaseous reactant to reaction temperature by introducing said reactant into the reactor and withdrawing preheated gas from the reactor; and (3) reactivating deactivated solids by introducing said reactivating gas into the reactor and withdrawing gaseous effluent from the reactor; and
    (c) concurrently operating said reactor zones such that, at any given time, the gaseous reactant is being preheated to reaction temperature in at least one reactor and said preheated gaseous reactant is being converted into said gaseous reaction product in at least one second reactor.

2. In a method for converting methane to higher hydrocarbon products wherein a gas comprising methane is contacted at a reaction temperature within the range of about 500° to 1000° C. with a quantity of solids comprising at least one reducible oxide of at least one metal which oxides are reduced when contacted with methane and produce higher hydrocarbon products and water and wherein solids comprising reduced metal oxide(s) are periodically contacted with an oxygen-containing gas to regenerate solids comprising said reducible oxide(s), the improvement which comprises:
    (a) providing the quantity of solids in relatively equal amounts in at least three reactor zones;
    (b) sequentially operating each reactor zone according to the cycle comprising: (1) introducing a gas comprising methane, preheated to reaction temperature, into the said reactor and withdrawing gaseous reaction products comprising higher hydrocarbons from the reactor; (2) preheating said gas comprising methane to reaction temperature by introducing said gas into the reactor and withdrawing preheated gas comprising methane from the reactor; and (3) regenerating solids comprising reducible metal oxides by introducing an oxygen-containing gas into the reactor and withdrawing gaseous effluent from the reactor; and
    (c) concurrently operating said reactor such that at any give time, the gas comprising methane is being preheated to reaction temperature in at least one first reactor, and said preheated gas comprising methane is being converted into hydrocarbon products in at least one second reactor.

3. The method of claim 2 wherein the gas comprising methane is purged from the reactor between the preheating and regenerating portions of said cycle by introducing a purge gas into the reactor said withdrawing purged gas from the reactor.

4. The method of claim 2, wherein the oxygen-containing gas is purged from the reactor between the regeneration and methane conversion portions of said cycle by introducing a purge gas into the reactor and withdrawing purged gas from the reactor.

5. The method of claim 3 wherein the oxygen-cotaining gas is purged from the reactor between the regeneration and methane conversion portions of said cycle by introducing a purge gas into the reactor and withdrawing purged gas from the reactor.

6. In a method for converting methane to higher hydrocarbon products wherein a gas comprising methane is contacted at a reaction temperature within the range of about 500° to 1000° C. with a quantity of solids comprising at least one reducible oxide of at least one metal which oxides are reduced when contacted with methane and produce higher hydrocarbon products and water and wherein solids comprising reduced metal oxide(s) are periodically contacted with an oxygen-containing gas to regenate solids comprising said reducible oxide(s), the improvement which comprises:

(a) providing the quantity of solids in relatively equal amounts in at least one module consisting of four reactor zones;

(b) sequentially operating each reactor zone of each said module according to the following cycle: (1) introducing and reacting a gas comprising methane, preheated to reaction temperature, with solids comprising reducible metal oxide(s) to produce higher hydrocarbon products and solids comprising reduced metal oxide(s) and withdrawing gaseous reaction product comprising higher hydrocarbon from a the reactor; (2) preheating a gas comprising methane to reaction temperature by contacting said gas with solids comprising reduced metal oxide(s), thereby cooling said solids; (3) purging the gas comprising methane from said cooled solids; (4) regenerating solids comprising reducible metal oxide(s) by contacting said cooled; purged solids with an oxygen-containing gas and withdrawing gaseous effluent from reactor; and (5) purging the oxygen-containing gas from said regenerated solids; and (c) concurrently operating the reactors of said module that such, at any given time, a gas comprising methane is being preheated to reaction temperature in at least one first reactor, said preheated gas is reacting to form higher hydrocarbon products in at least one second reactor, solids comprising reducible metal oxide(s) are being regenerated in at least one third reactor, and at least one fourth reactor is being purged.

7. In a method for dehydrogenating dehydrogenatable hydrocarbons wherein a gas comprising said hydrocarbon is contacted at a reaction temperature within the range of about 500° to 1000° C. with a quantity of solids comprising at least one reducible oxide of at least one metal which oxides are reduced when contacted with hydrocarbon and produce dehydrogenated hydrocarbon products and water and wherein solids comprising reduced metal oxide(s) are periodically contacted with an oxygen-containing gas to regenerate solids comprising said reducible oxide(s), the improvement which comprises:

(a) providing the quantity of solids in relatively equal amounts in at least three reactor zones;

(b) sequentially operating each reactor according to the cycle comprising: (1) introducing a gas comprising said hydrocarbon preheated to reaction temperature, into the reactor and withdrawing gaseous reaction products comprising dehydrogenated hydrocarbons from the reactor; (2) preheating said gas comprising hydrocarbon to reaction temperature by introducing said gas into the reactor and withdrawing preheated gas comprising dehydrogenatable hydrocarbons from the reactor; and (3) regenerating solids comprising reducible metal oxides by introducing an oxygen-containing gas into the reactor and withdrawing gaseous effluent from the reactor; and (c) concurrently operating said reactor zones such that at any given time, the gas comprising said hydrocarbon is being preheated to reaction temperature in at least one first reactor, and said preheated gas is being converted into dehydrogenated hydrocarbon products in at least one second reactor.

8. The method of claim 7 wherein the gas comprising dehydrogenatable hydrocarbon is purged from the reactor between the preheating and regenerating portions of said cycle by introducing a purge gas into the reactor and withdrawing purged gas from the reactor.

9. The method of claim 7 wherein the oxygen-containing gas is purged from the reactor between the regeneration and hydrocarbon conversion portions of said cycle by introducing a purge gas into the reactor and withdrawing purged gas from the reactor.

10. The method of claim 8 wherein the oxygen-containing gas is purged from the reactor between the regeneration and hydrocarbon conversion portions of said cycle by introducing a purge gas into the reactor and withdrawing purged gas from the reactor.

* * * * *